United States Patent
Kai et al.

(10) Patent No.: US 8,854,206 B2
(45) Date of Patent: Oct. 7, 2014

(54) SAMPLE MEASURING DEVICE AND SAMPLE MEASURING SYSTEM

(75) Inventors: Akinori Kai, Kyoto (JP); Atsushi Wada, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 102 days.

(21) Appl. No.: 13/458,694

(22) Filed: Apr. 27, 2012

(65) Prior Publication Data

US 2012/0274443 A1    Nov. 1, 2012

(30) Foreign Application Priority Data

Apr. 28, 2011   (JP) .................... 2011-100409

(51) Int. Cl.
G08B 1/08 (2006.01)
A61B 5/00 (2006.01)
A61B 5/145 (2006.01)

(52) U.S. Cl.
CPC ........... *A61B 5/14532* (2013.01); *A61B 5/0002* (2013.01)
USPC ...................... 340/539.12; 340/5.61; 600/300

(58) Field of Classification Search
USPC ................. 340/12.5, 539.12; 705/75; 702/18; 600/300
See application file for complete search history.

(56) References Cited

U.S. PATENT DOCUMENTS 7,240,036 B1 * 7/2007 Mamdani et al. ................ 705/75
8,131,478 B2 * 3/2012 Kai ................. 702/19

2010/0137697 A1   6/2010 Kubo et al.
2010/0312082 A1  12/2010 Batman et al.
2011/0063094 A1   3/2011 Meiertoberens et al.

FOREIGN PATENT DOCUMENTS

| CN | 101821722 A | 9/2010 |
| EP | 2 001 188 A1 | 12/2008 |
| WO | 2008/136437 A1 | 11/2008 |
| WO | 2009/005950 A2 | 1/2009 |

OTHER PUBLICATIONS

An Office Action issued by the State Intellectual Property Office of People's Republic of China on Apr. 28, 2013, which corresponds to Chinese Patent Application No. 201210129971.7 and is related to U.S. Appl. No. 13/458,694.
A Chinese document "Service safety, three levels are defined in bluetooth standard"; I136-106; Mar. 31, 2005.
The European Search Report with mailing date of Aug. 7, 2012: EP Application No. 12 16 5998.

* cited by examiner

*Primary Examiner* — Steven Lim
*Assistant Examiner* — Kaleria Knox
(74) *Attorney, Agent, or Firm* — Studebaker & Brackett PC

(57) ABSTRACT

A sample measuring device according to the present invention includes a measuring unit for performing measurement with respect to a particular component contained in a sample, a measurement data storage unit for storing measurement data obtained by the measuring unit, a display unit for displaying the measurement data, a sensor strip detector for detecting insertion and removal of a sensor strip to which the sample is applied, and a first data transmitter/receiver for transmitting the measurement data via wireless communication. The first data transmitter/receiver performs initial authentication process for wireless communication after insertion of the sensor strip is detected by the sensor strip detector.

12 Claims, 12 Drawing Sheets

SAMPLE MEASURING DEVICE AND SAMPLE MEASURING SYSTEM

BACKGROUND OF THE INVENTION

1. Field of the Invention

The present invention relates to a sample measuring device and a sample measuring system.

2. Description of the Related Art

FIG. 14 illustrates an example of sample measuring system (see Patent Document 1, for example). The sample measuring system 900 shown in the figure comprises a sample measuring device 91 and a personal computer 93 (hereinafter referred to as "PC 93"). For instance, the sample measuring device 91 is a self-monitoring blood glucose meter (SMBG meter) which enables users to measure their own blood glucose levels. Measurement by the sample measuring device 91 is performed by inserting a sensor strip 92 into the sample measuring device 91 and applying blood to the sensor strip 92. Before or after the measurement, the sample measuring device 91 is connected to the PC 93 via a cable 94. The measurement data obtained by the sample measuring device 91 is sent to the PC 93 via the cable 94 and stored in the PC 93. The PC 93 is capable of storing data of a plurality of measurements. The stored measurement data can be checked by e.g. a doctor so that the doctor can provide treatment or medicine suitable for the diabetes symptoms of the user.

However, it is troublesome to connect the sample measuring device 91 and the PC 93 via the cable 94 at each time of measurement. When the user fails to connect the sample measuring device 91 via the cable 94, the measurement data is not stored in the PC 93. In such a case, it may be difficult for the doctor to provide the user with proper treatment or medicine.

Patent Document 1: JP-A1-2008-136437

SUMMARY OF THE INVENTION

The present invention has been proposed under the circumstances described above. It is therefore an object of the present invention to provide a sample measuring device and a sample measuring system capable of reducing burdens on the user.

According to a first aspect of the present invention, there is provided a sample measuring device including a measuring unit for performing measurement with respect to a particular component contained in a sample, a measurement data storage unit for storing measurement data obtained by the measuring unit, a display unit for displaying the measurement data, a sensor strip detector for detecting insertion and removal of a sensor strip to which the sample is applied, and a first data transmitter/receiver for transmitting the measurement data via wireless communication. The first data transmitter/receiver performs initial authentication process for wireless communication after insertion of the sensor strip is detected by the sensor strip detector.

In a preferred embodiment of the present invention, when insertion of the sensor strip is detected by the sensor strip detector, the sample measuring device switches from a standby state in which the measurement is not possible to an operation state in which the measurement is possible.

In a preferred embodiment of the present invention, when removal of the sensor strip is detected by the sensor strip detector, the sample measuring device switches from the operation state to the standby state.

In a preferred embodiment of the present invention, the sample measuring device further includes an authentication code storage portion for storing an authentication code to be used for the initial authentication process, and the authentication code is displayed on the display unit in the initial authentication process.

In a preferred embodiment of the present invention, the sample measuring device further includes an authentication code print portion in which an authentication code to be used for the initial authentication process is printed.

In a preferred embodiment of the present invention, the authentication code is a product identification code.

In a preferred embodiment of the present invention, when the first data transmitter/receiver detects presence of a communication device with which wireless connection can be established, the communication device is identified and indicated on the display unit as a possible connection target device.

In a preferred embodiment of the present invention, when the first data transmitter/receiver detects presence of a plurality of communication devices with which wireless connection can be established, the communication devices are identified and indicated on the display unit periodically one by one as possible connection target devices.

In a preferred embodiment of the present invention, the first data transmitter/receiver performs the initial authentication process with respect to one of the plurality of communication devices which is being indicated on the display unit when there is a change in a detection state of the sensor strip detector.

In a preferred embodiment of the present invention, the change in the detection state of the sensor strip detector is due to removal of the sensor strip from the sample measuring device.

In a preferred embodiment of the present invention, the change in the detection state of the sensor strip is due to removal and subsequent re-insertion of the sensor strip with respect to the sample measuring device.

In a preferred embodiment of the present invention, the first data transmitter/receiver performs wireless communication based on Bluetooth (registered trademark) standard.

In a preferred embodiment of the present invention, the particular component is blood sugar, and the sample measuring device is structured as a self-monitoring blood glucose meter.

According to a second aspect of the present invention, there is provided a sample measuring system including the sample measuring device provided according to the first aspect of the present invention, and a communication device including a second data transmitter/receiver which is a target for the initial authentication process performed by the first data transmitter/receiver of the sample measuring device.

In a preferred embodiment of the present invention, the communication device includes an input unit for inputting an authentication code provided by the sample measuring device.

According to the present invention, when the user inserts the sensor strip into the sample measuring device to perform measurement, whether or not the pairing has been completed is determined automatically, and if not completed, the pairing process occurs automatically. Thus, establishment of the connection between the sample measuring device and the communication device does not require any special work by the user. The user can transmit measurement data from the sample measuring device to the communication device without worrying about whether or not the connection with the communication device has been established.

Other features and advantages of the present invention will become more apparent from detailed description given below with reference to the accompanying drawings.

DETAILED DESCRIPTION OF THE PREFERRED EMBODIMENTS

Preferred embodiments of the present invention are described below with reference to the accompanying drawings.

Figure 1:
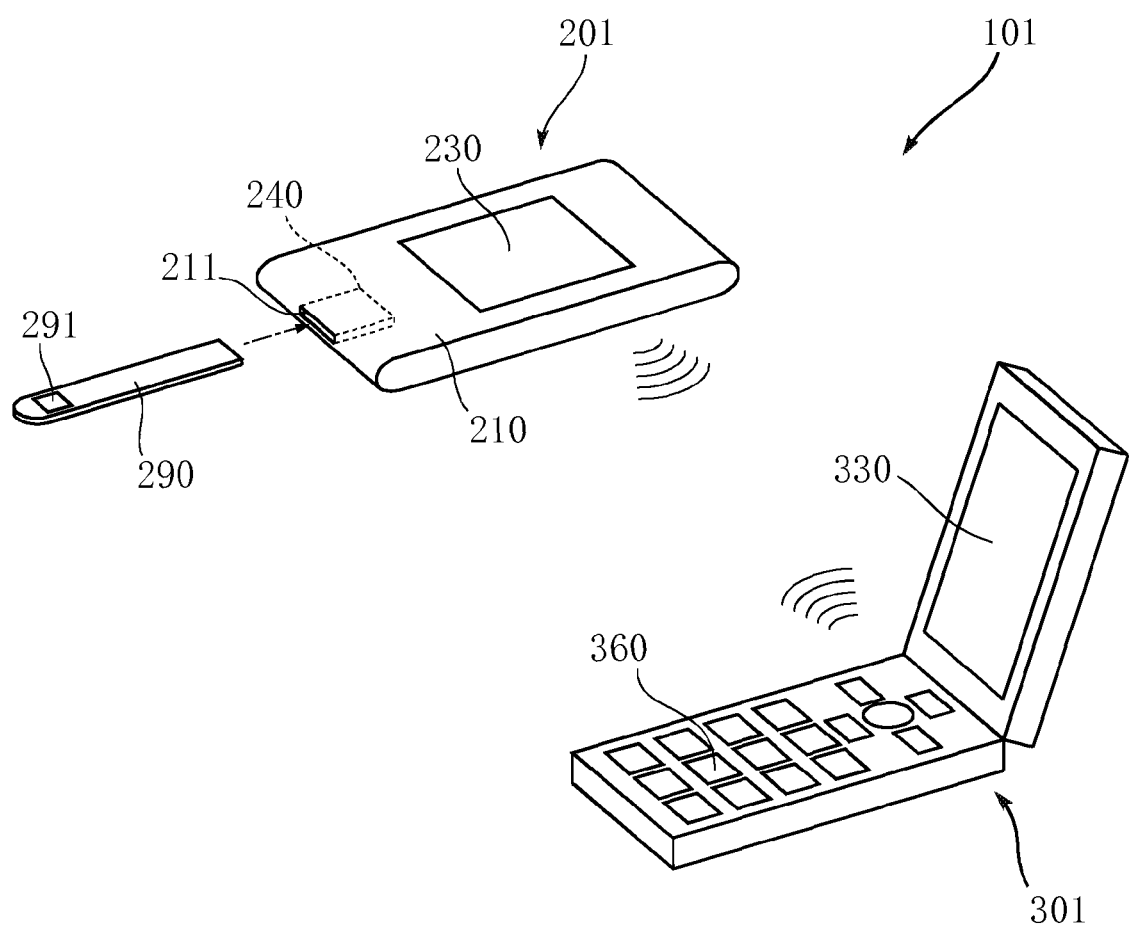
FIG. 1 is a perspective view showing an example of sample measuring device and sample measuring system according to the present invention.

FIG. 1 shows an example of sample measuring device and sample measuring system according to the present invention. The sample measuring system 101 of this embodiment includes a sample measuring device 201 and a communication device 301.

Figure 2:
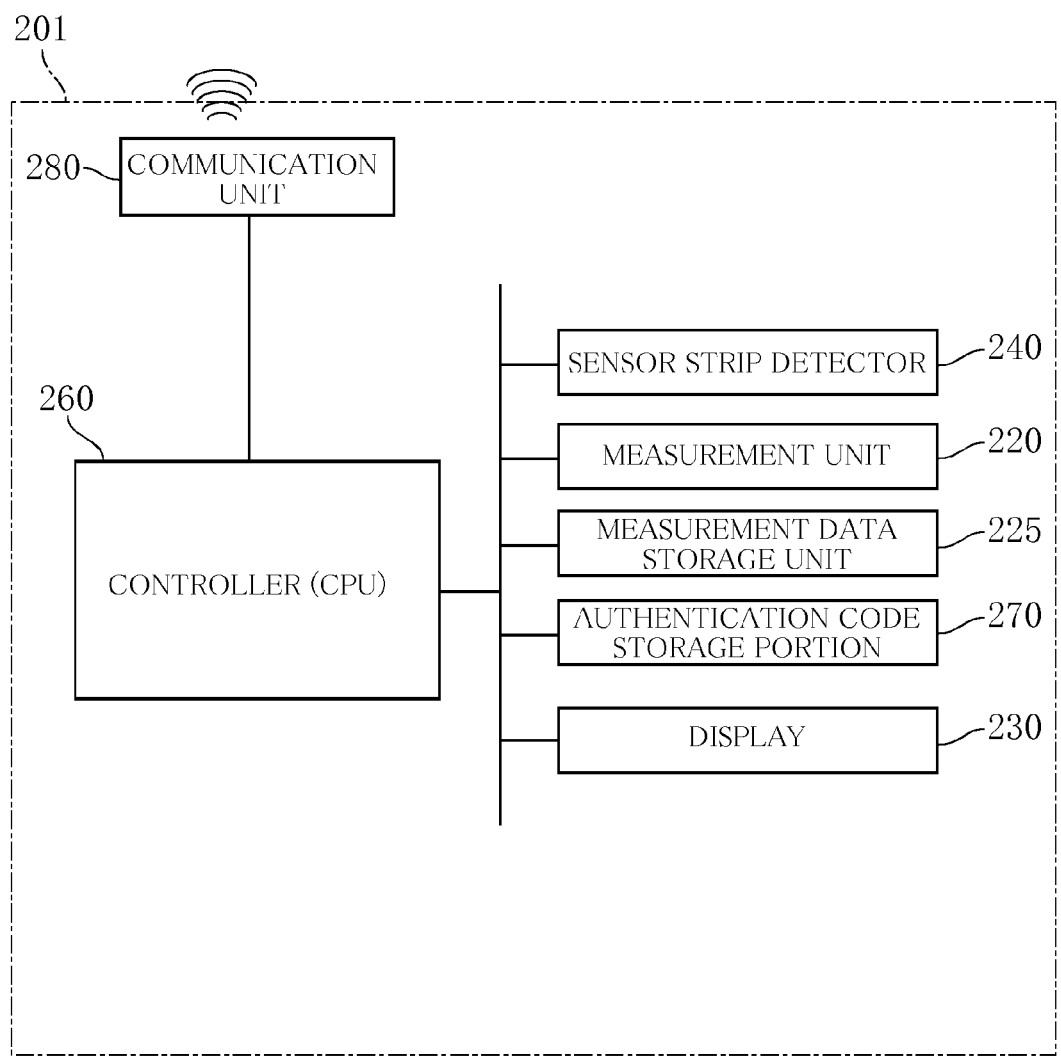
FIG. 2 is a system block diagram of the example of sample measuring device according to the present invention.

The sample measuring device 201 is structured as e.g. a self-monitoring blood glucose meter (SMBG meter) used for self-measurement of blood glucose level by the user. As shown in FIGS. 1 and 2, the sample measuring device 201 includes a case 210, a measurement unit 220, a measurement data storage unit 225, a display 230, a sensor strip detector 240, a controller 260, an authentication code storage portion 270 and a communication unit 280. The sample measuring device 201 uses a sensor strip 290 for measurement. The sensor strip 290 has a sample application portion 291. To perform measurement with the sample measuring device 201, the sensor strip 290 is inserted into the insertion port 211, and blood of the user is applied to the sample application portion 291.

The case 210 is made of e.g. resin and defines the outer configuration of the sample measuring device 201. The case 210 has the insertion port 211 into which the sensor strip 290 is to be inserted. The sensor strip detector 240 is provided behind the insertion port 211 and detects the insertion of the sensor strip 290. For instance, the sensor strip detector 240 may comprise a mechanical lever (not shown) which pivots when the sensor strip 290 is inserted or a pair of detection electrodes (not shown) which are electrically connected to each other when the sensor strip 290 is inserted.

The measurement unit 220 serves to measure the blood glucose level. For instance, the measurement unit 220 includes a terminal (not shown) to be electrically connected to the sensor strip 290 to which blood has been applied and measures the blood glucose level by an electrical method. The measurement data storage unit 225 comprises e.g. a memory and stores the measurement data obtained by the measurement unit 220. The display 230 is an example of the display unit according to the present invention and serves to show measurement data and so on. For instance, the display 230 comprises a liquid crystal display panel.

The controller 260 controls each part of the sample measuring device 201 during the measurement operation, and comprises e.g. a CPU.

The communication unit 280 is an example of the first data transmitter/receiver according to the present invention and serves to transmit and receive data via wireless communication. In this embodiment, the communication unit 280 performs wireless communication based on the Bluetooth standard. Thus, the communication unit 280 is capable of performing interactive wireless communication.

The authentication code storage portion 270 serves to store a passkey (authentication code) necessary for the pairing process (initial authentication process) for establishing a connection between the sample measuring device 201 and the communication device 301. In the wireless communication based on the Bluetooth standard, after the pairing process is performed once, communication between the paired devices is allowed when the devices are located within a predetermined distance from each other.

Figure 3:
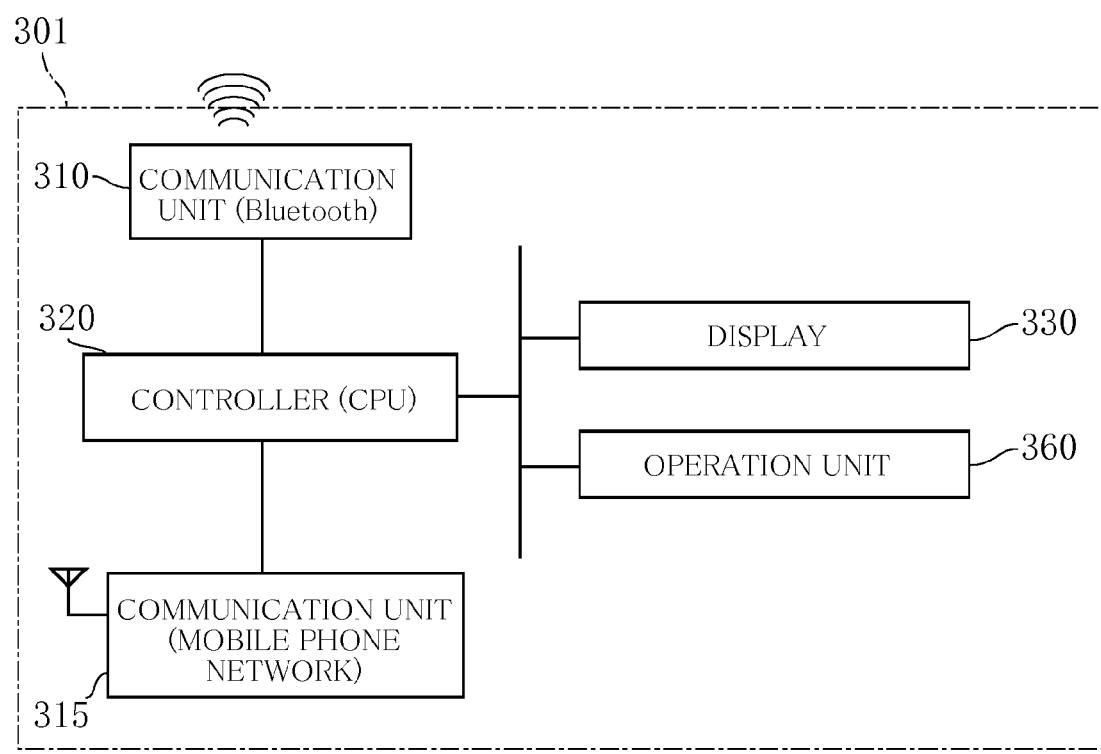
FIG. 3 is a system block diagram of a communication device used for the example of sample measuring system according to the present invention.

The communication device 301 is e.g. a mobile phone and has a function to receive and store the measurement data transmitted from the sample measuring device 201 and transmit the measurement data to e.g. a server device (not shown) via a public communication network. As shown in FIGS. 1 and 3, the communication device 301 includes a communication unit 310, a communication unit 315, a controller 320, a display 330 and an operation unit 360.

The communication unit 310 is an example of the second data transmitter/receiver according to the present invention and serves to transmit and receive data via wireless communication. In this embodiment, the communication unit 310 performs wireless communication based on the Bluetooth standard. Thus, the communication unit 310 is capable of performing interactive wireless communication. The communication unit 315 serves to make access to a mobile phone network via wireless communication. Thus, the communication device 301 is capable of making access to the mobile phone network and to the Internet via the mobile phone network.

The controller 320 controls each portion of the communication device 301 during the measurement operation, and comprises e.g. a CPU. For instance, the display 330 comprises a liquid crystal display panel. The operation unit 360 comprises e.g. dial keys or arrow keys.

The operation of the sample measuring device 201 and the sample measuring system 101 are described below with reference to FIGS. 4-9.

Figure 4:
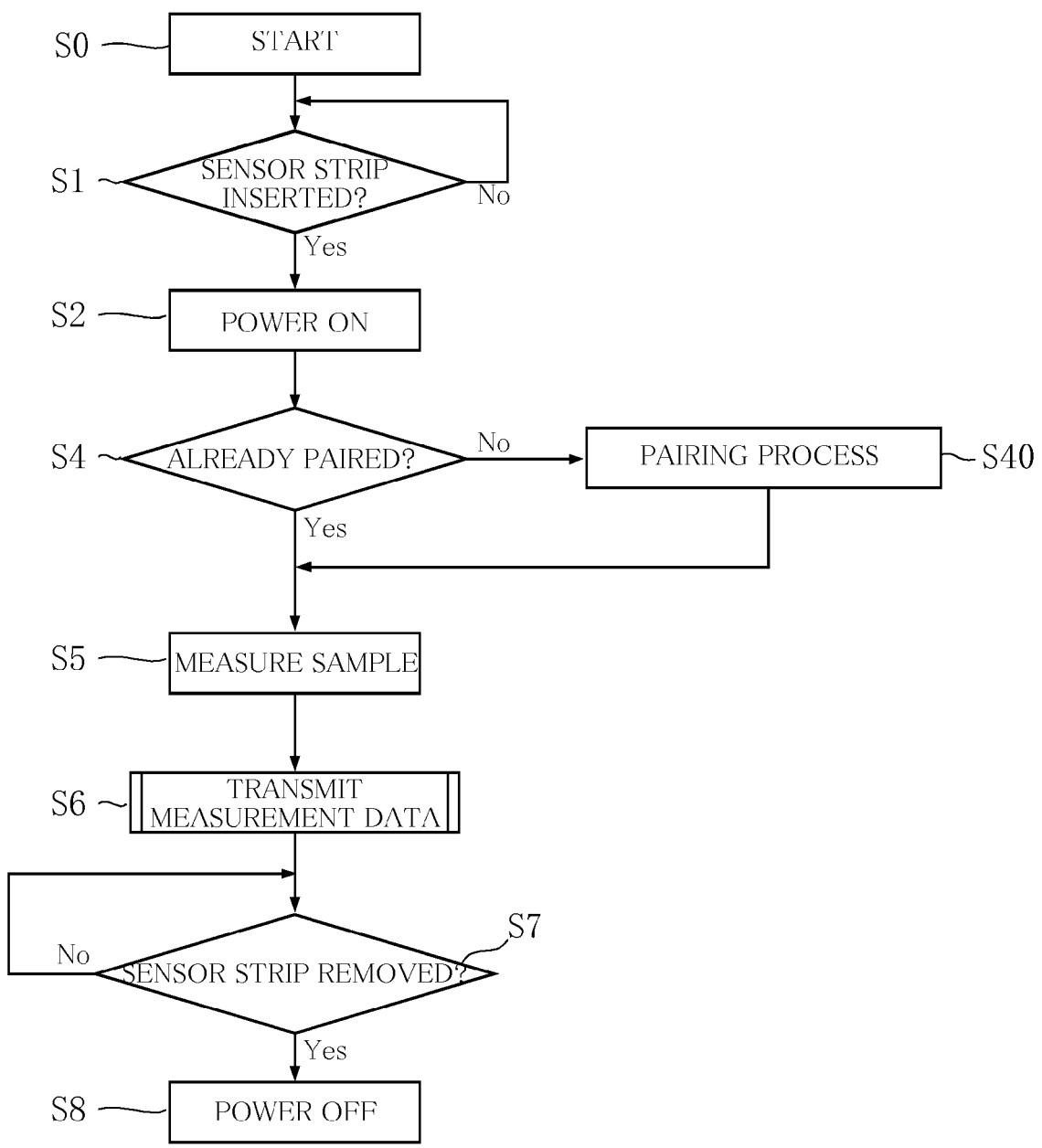
FIG. 4 is a flowchart showing the operation of the example of sample measuring device according to the present invention.

FIG. 4 is a flowchart showing the operation of the sample measuring device 201. The operation of the sample measuring device 201 starts from Step S0. In Step S0, the display 230 is in a non-display state, and the sample measuring device 201 is in a so-called "power-off state". In this state, however, the sensor strip detector 240 is in a state capable of detecting the sensor strip 290. Specifically, when the sensor strip detector 240 is designed to detect the sensor strip 290 by an electrical method, the sensor strip detector 240 is supplied with electric power. When the sensor strip detector 240 does not require electric power, power supply may be completely shut off. This state, which corresponds to a so-called "power-off state" and in which the sensor strip detector 240 is ready to detect, is defined as the "standby state" in the present invention.

Figure 6:
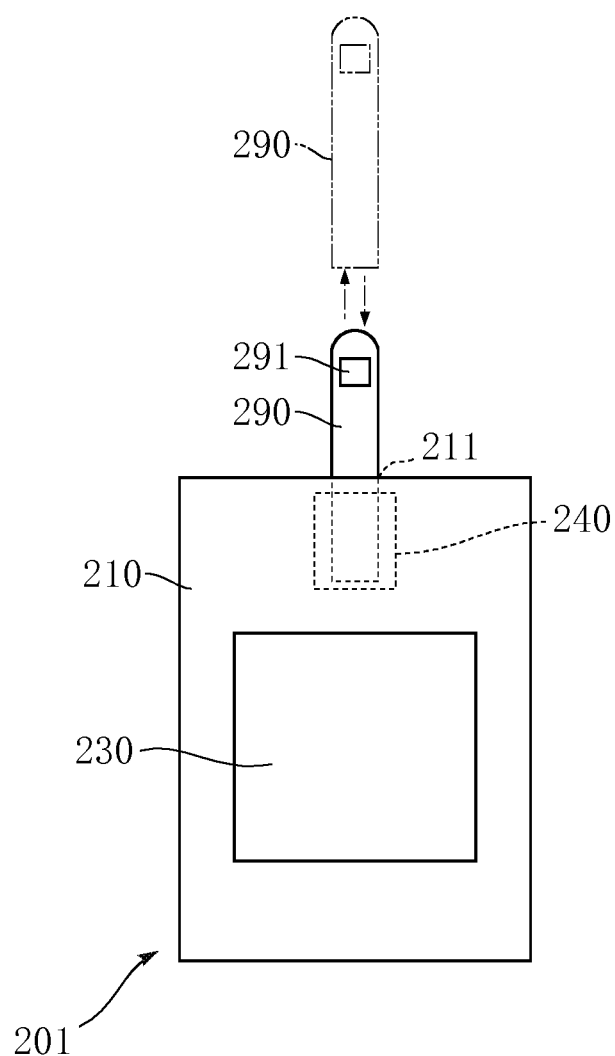
FIG. 6 is a front view of the example of sample measuring device, showing the insertion and removal of a sensor strip.

Then, in Step S1, whether or not the sensor strip 290 is inserted is detected by the sensor strip detector 240. When the sensor strip 290 is inserted as shown in FIG. 6, an insertion detection signal is transmitted from the sensor strip detector 240 to the controller 260 (see FIG. 2). Upon receiving the signal, the controller 260 starts to supply electric power to the entirety of the sample measuring device 201. Thus, in Step S2 in FIG. 4, the sample measuring device 201 switches to a so-called "power-on state". This state is defined as the "operation state" in the present invention.

Then, in Step S4, whether or not the pairing has been completed is determined. Specifically, the controller 260 receives a status signal of the communication unit 280, and, when it is determined that the pairing has not been completed, causes the pairing process of Step S40 to start. Instead of this automatic proceeding from Step S4 to Step S40 based on the determination by the controller 260, the sample measuring device 201 may be designed such that the process proceeds from Step S4 to Step S40 when the sensor strip 290 is once removed and then inserted again by the user.

Figure 5:
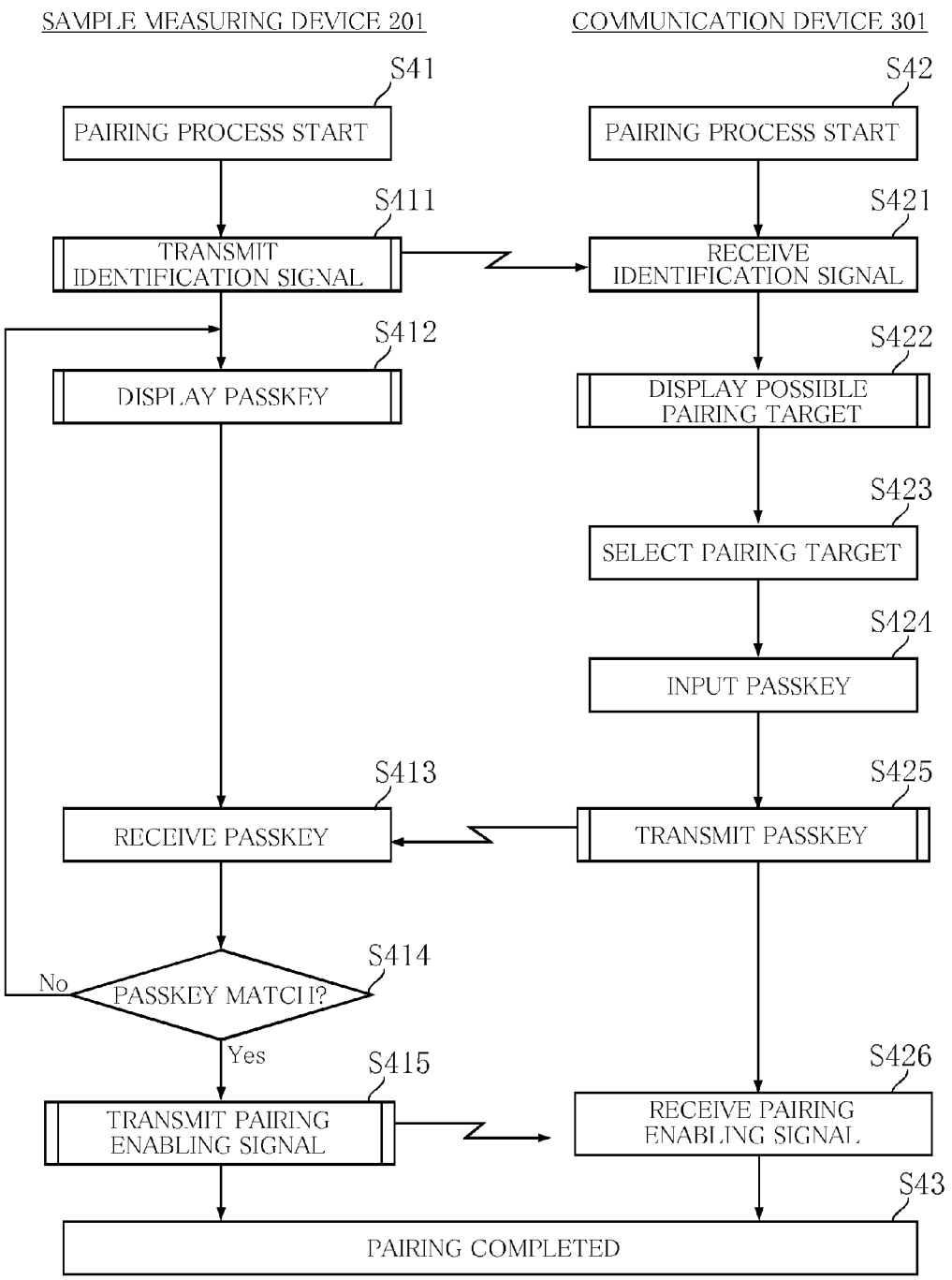
FIG. 5 is a flowchart showing the pairing process of the example of sample measuring system according to the present invention.

FIG. 5 is a flowchart showing the pairing process between the sample measuring device 201 and the communication device 301. In the sample measuring device 201, the pairing process is started in Step S41. In the communication device 301, the pairing process is started in Step S42 by the user's predetermined operation using e.g. the operation unit 360.

Figure 7:
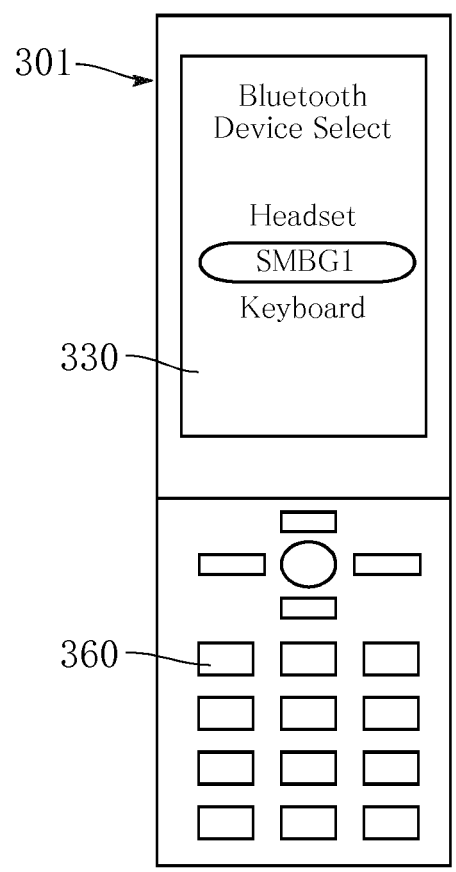
FIG. 7 is a front view of a display in a step for selecting a pairing target device in the pairing process of the example of sample measuring system according to the present invention.

In Step S411, an identification signal is sent out from the communication unit 280 of the sample measuring device 201. The identification signal is a signal for allowing the communication device 301 to detect the presence of the sample measuring device 201. When the communication unit 310 of the communication device 301 receives the identification signal in Step S421, the controller 320 displays on the display 330 the information contained in the identification signal in Step S422, as shown in FIG. 7. In this embodiment, the identification signal contains the name of the sample measuring device 201, which is "SMBG1" in this example, so that "SMBG1" is shown on the display 330 as a possible pairing target device.

Then, in Step S423 shown in FIG. 5, the pairing target device is selected. Specifically, in this embodiment, names of a plurality of devices which can be paired with the communication device 301, including "SMBG1", are listed on the display 330 as possible pairing target devices, as shown in FIG. 7. In this instance, the frame in the display 330 which surrounds one of the names of the devices can be moved up and down by e.g. pressing an arrow key of the operation unit 360. Thus, by positioning the frame around the name of the desired device and then pressing the decision button of the operation unit 360, the desired device is selected as the pairing target device for the communication device 301. In this embodiment, "SMBG1" is selected.

Figure 8:
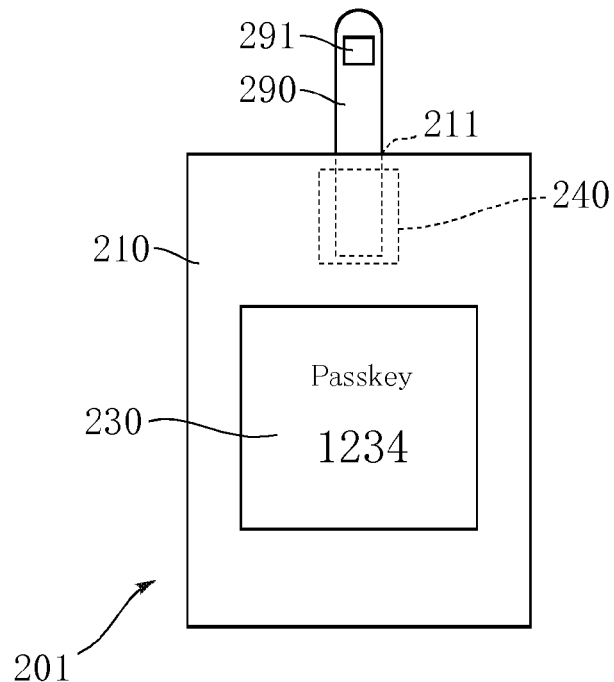
FIG. 8 is a front view of a display in a step for showing a passkey in the pairing process of the example of sample measuring system according to the present invention.
Figure 9:
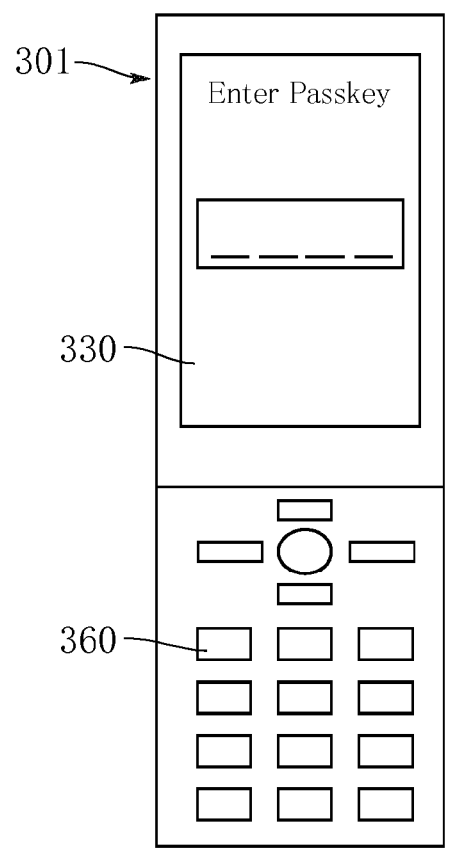
FIG. 9 is a front view of a display in a step for inputting a passkey in the pairing process of the example of sample measuring system according to the present invention.

When selection of the pairing target device is completed in Step S423 in FIG. 5, input of the passkey is requested in Step S424 in the communication device 301. On the other hand, in the sample measuring device 201, when Step S411 is completed, the passkey is shown in Step S412. Specifically, the passkey stored in the authentication code storage portion 270 is shown on the display 230 of the measuring device 201 as shown in FIG. 8 in Step S412, while a message to prompt the user to input the passkey is shown on the display 330 of the communication device 301 as shown in FIG. 9 in Step S424. In Step S424, the passkey shown on the display 230 is inputted into the communication device 301 by using e.g. numeric keys of the operation unit 360.

Then, in Step S425, the controller 320 of the communication device 301 sends out the passkey, inputted in Step S424, from the communication unit 310. In Step S413, the sample measuring device 201 receives the passkey through the communication unit 280. Then, in Step S414, the passkey received is checked against the passkey stored in the authentication code storage portion 270. When these keys match with each other, the sample measuring device 201 sends out a pairing enabling signal from the communication unit 280 in Step S415. The communication device 301 receives the pairing enabling signal through the communication unit 310 in Step S426. After the pairing process is completed in this way in Step S43, the sample measuring device 201 and the communication device 301 can perform interactive wireless communication based on the Bluetooth standard.

Thereafter, in Step S5 in FIG. 4, the blood glucose level is measured by the measurement unit 220. The blood glucose level data obtained is stored in the measurement data storage unit 225. In Step S6, the blood glucose level data is transmitted from the communication unit 280 to the communication device 301. This data transmission may be performed automatically when the connection between the sample measuring device 201 and the communication device 301 is established or may be performed by the selection operation by the user. Thereafter, when removal of the sensor strip 290 is detected by the sensor strip detector 240 in Step S7, the sample measuring device 201 is switched to the power-off state in Step S8.

The advantages of the sample measuring device 201 and the sample measuring system 101 are described below.

According to the present invention, when the user inserts the sensor strip 290 into the sample measuring device 201 to perform measurement, whether or not the pairing has been completed is determined automatically, and if not completed, the pairing process occurs automatically. Thus, establishment of the connection between the sample measuring device 201 and the communication device 301 does not require any special work by the user. The user can transmit measurement data from the sample measuring device 201 to the communication device 301 without worrying about whether or not the connection with the communication device 301 has been established.

With the use of the wireless communication based on the Bluetooth standard for data transmission between the sample measuring device 201 and the communication device 301, when the sample measuring device 201 and the communication device 301 are within a predetermined distance from each other, the data transmission can be started automatically, so that the user does not need to worry about whether or not the connection has been established. The sample measuring device 201 switches between the power-on state and the power-off state in accordance with the insertion and removal of the sensor strip 290. This means that switching of the sample measuring device 201 between the power-on state and the power-off state occurs in accordance with the user's intention to perform measurement, just by the operation essential to the measurement, and without the need for any additional operation. Thus, according to the sample measuring device 201, the measurement and the communication with the communication device 301 can be started easily as the user desires.

Since the passkey stored in the authentication code storage portion 270 is shown on the display 230 of the sample measuring device 201, the user does not need to check the manual or the like of the sample measuring device 201 for the passkey. Since the passkey generally consists of a relatively small number of alphanumeric characters, the display 230 does not need to be made large to show the passkey.

FIGS. 10-13 show variations of the sample measuring device and the sample measuring system according to the present invention. In these figures, the elements which are identical or similar to those of the foregoing embodiment are designated by the same reference signs as those used for the foregoing embodiment.

Figure 10:
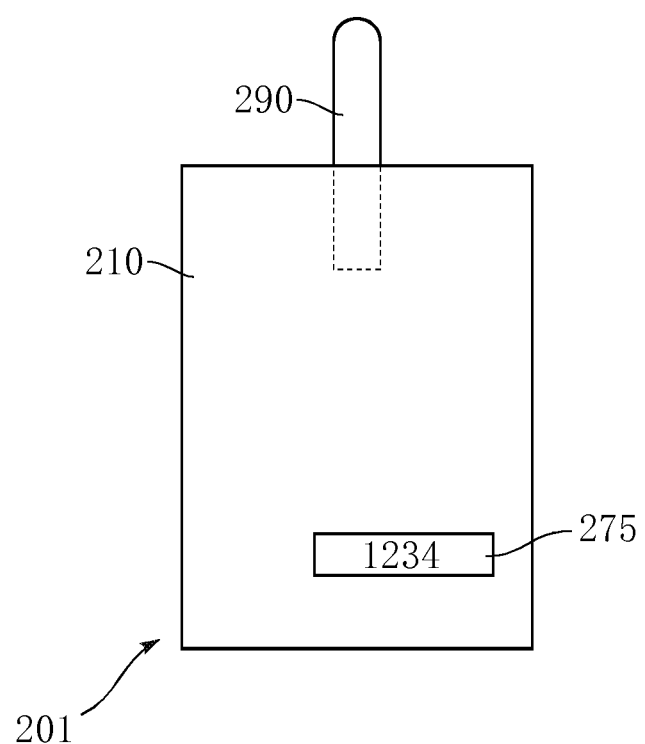
FIG. 10 is a rear view of a variation of sample measuring device according to the present invention.

FIG. 10 shows a variation of the sample measuring device 201. The sample measuring device 201 of this variation includes an authentication code print portion 275 instead of the authentication code storage portion 270. The authentication code print portion 275 comprises e.g. a label which is attached to the back surface of the case 210 and on which the passkey is printed. In the pairing process according to this variation, displaying the passkey in Step S412 is performed not at the display 230 but at the authentication code print portion 275. In Step S424, the user inputs the passkey printed on the authentication code print portion 275.

According to this variation again, the user can transmit measurement data from the sample measuring device 201 to the communication device 301 without worrying about whether the connection with the communication device 301 has been established. Further, reading the passkey printed on the authentication code print portion 275 such as a label may be easier for some users, such as elderly people, than reading the passkey shown on the display.

Figure 11:
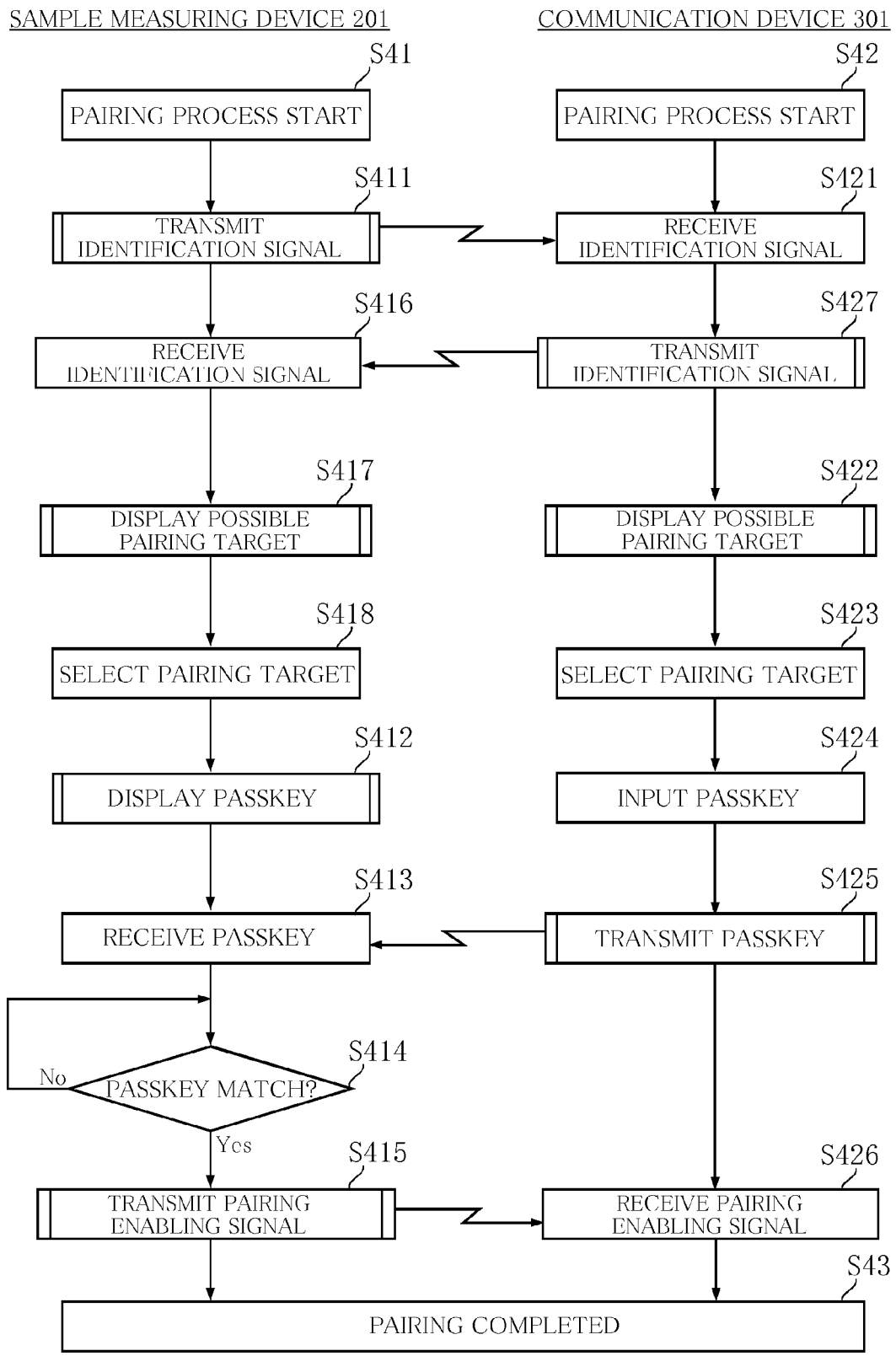
FIG. 11 is a flowchart showing a variation of pairing process of the sample measuring system according to the present invention.
Figure 12:
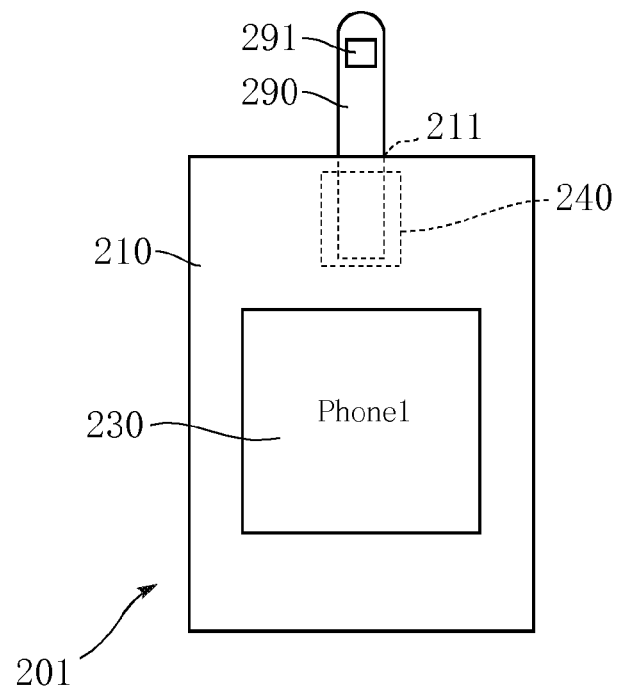
FIG. 12 is a front view showing an example of display of the sample measuring device in a step for selecting a pairing target device in the pairing process shown in FIG. 11.

FIG. 11 shows a variation of the pairing process of the sample measuring system 101. In this variation, selection of the pairing target device is performed not only by the communication device 301 but also by the sample measuring device 201. Specifically, the communication device 301 sends out an identification signal in Step S427. The identification signal sent out by the communication device 301 is received by the sample measuring device 201 in Step S416, and the name of the communication device 301 is shown in Step S417 on the display 230 of the sample measuring device 201. In this example, the name "Phone 1" of the communication device 301 is shown. In this step, when there are other possible target devices which can be paired with the sample measuring device 201, a plurality of device names, including the name "Phone 1", are shown on the display 230 alternately, each for a certain period of time. In Step S418 shown in FIG. 11, the user selects the desired pairing target device by once pulling out and then inserting again the sensor strip 290 when the name of the desired pairing target device ("Phone 1" in this example) is shown on the display 230.

Figure 13:
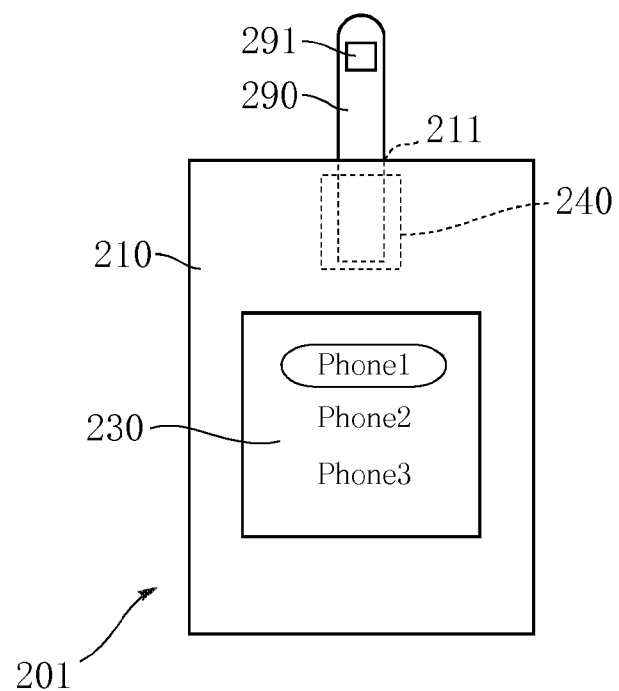
FIG. 13 is a front view showing another example of display of the sample measuring device in a step for selecting a pairing target device in the pairing process shown in FIG. 11.
Figure 14:
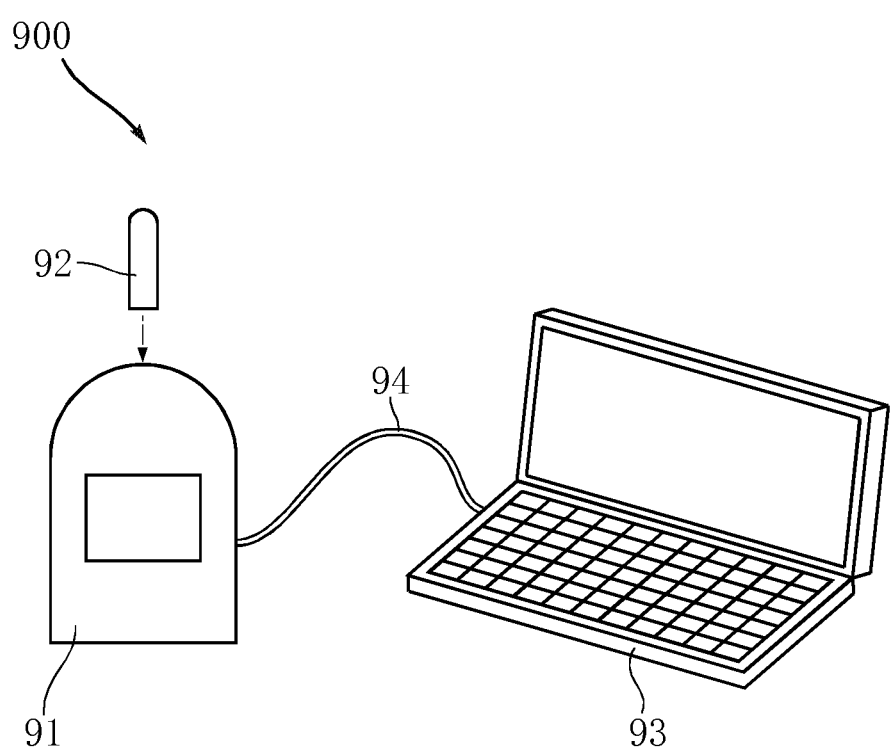
FIG. 14 is a perspective view showing an example of conventional sample measuring device and sample measuring system.

FIG. 13 shows another way of displaying the names of pairing target devices in Step S417. In this instance, the names of a plurality of possible pairing target devices are shown as a list on the display 230. In the display 230, there is shown a frame surrounding one of the names of the possible pairing target devices. The frame moves periodically to alternately surround each of the names of the possible pairing target devices. In Step S418 shown in FIG. 11, the user selects the desired pairing target device by once pulling out and then inserting again the sensor strip 290 when the name of the desired pairing target device ("Phone 1" in this example) is surrounded by the frame.

According to this variation again, the user can transmit measurement data from the sample measuring device 201 to the communication device 301 without worrying about whether the connection with the communication device 301 has been established. Moreover, when there a plurality of devices of the type similar to the communication device 301 are present, pairing the sample measuring device 201 erroneously with an undesired communication device is prevented more reliably.

The sample measuring device and sample measuring system according to the present invention is not limited to the foregoing embodiments. The specific structure of each part of the sample measuring device and sample measuring system according to the present invention can be varied in design in many ways.

The communication device according to the present invention is not limited to a mobile phone, and any devices which can perform wireless communication with the sample measuring device can be used. For instance, a personal computer designed to transmit and receive data via wireless communication based on the Bluetooth standard may be used as the communication device. Moreover, the sample measuring device according to the present invention is not limited to a SMBG meter. The invention is applicable to various devices for performing measurement for which transmission of measurement data to a communication device or collection of measurement data via a communication device is desirable. The wireless communication in the present invention is not limited to that based on the Bluetooth standard, and any kind of wireless communication can be used as long as it can realize data transmission and reception between the sample measuring device and the communication device.

The invention claimed is:

1. A sample measuring device comprising:
   a measuring unit to perform measurement with respect to a particular component contained in a sample;
   a measurement data storage unit for storing measurement data obtained by the measuring unit;
   a display unit to display the measurement data;
   a sensor strip detector to detect insertion and removal of a sensor strip to which the sample is applied; and
   a first data transmitter/receiver to transmit the measurement data via wireless communication;
   wherein the first data transmitter/receiver is configured to perform initial authentication process for wireless communication with a communication device after insertion of the sensor strip is detected by the sensor strip detector,
   wherein, when the first data transmitter/receiver detects presence of one or a plurality of communication devices with which wireless connection may be established, the one or the plurality of communication devices are identified and indicated on the display unit as a possible connection target device,
   the sample measuring device is configured to established communication with the communication device selected as the target device and to transmit the measurement data to the target device when the insertion of the sensor strip has been detected, and wherein the particular component is blood sugar, and the sample measuring device is structured as a self-monitoring blood glucose meter.

2. The sample measuring device according to claim 1, wherein, when insertion of the sensor strip is detected by the sensor strip detector, the sample measuring device switches from a standby state in which the measurement is not possible to an operation state in which the measurement is possible.

3. The sample measuring device according to claim 2, wherein, when removal of the sensor strip is detected by the sensor strip detector, the sample measuring device switches from the operation state to the standby state.

4. The sample measuring device according to claim 1, further comprising an authentication code storage portion for storing an authentication code to be used for the initial authentication process, wherein the authentication code is displayed on the display unit in the initial authentication process.

5. The sample measuring device according to claim 1, further comprising an authentication code print portion in which an authentication code to be used for the initial authentication process is printed.

6. The sample measuring device according to claim 5, wherein the authentication code is a product identification code.

7. The sample measuring device according to claim 1, wherein the first data transmitter/receiver performs the initial authentication process with respect to the target device from the plurality of communication devices which is being indicated on the display unit when there is a change in a detection state of the sensor strip detector.

8. The sample measuring device according to claim 7, wherein the change in the detection state of the sensor strip detector is due to removal of the sensor strip from the sample measuring device.

9. The sample measuring device according to claim 8, wherein the change in the detection state of the sensor strip is due to removal and subsequent re-insertion of the sensor strip with respect to the sample measuring device.

10. The sample measuring device according to claim 1, wherein the first data transmitter/receiver performs wireless communication based on Bluetooth (registered trademark) standard.

11. A sample measuring system comprising:
the sample measuring device as set forth in claim 1; and
a communication device including a second data transmitter/receiver which is a target for the initial authentication process performed by the first data transmitter/receiver of the sample measuring device.

12. The sample measuring system according to claim 11, wherein the communication device includes an input unit for inputting an authentication code provided by the sample measuring device.

* * * * *